(12) United States Patent
Nozaki et al.

(10) Patent No.: US 8,042,604 B2
(45) Date of Patent: Oct. 25, 2011

(54) TEMPERATURE REGULATING MEMBER

(75) Inventors: Takayuki Nozaki, Chiba (JP); Kazutoshi Kan, Kawagoe (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/776,068

(22) Filed: Jul. 11, 2007

(65) Prior Publication Data

US 2008/0029247 A1    Feb. 7, 2008

(30) Foreign Application Priority Data

Aug. 2, 2006    (JP) ................................. 2006-210462

(51) Int. Cl.
    *F28D 20/00*        (2006.01)
(52) U.S. Cl. ........ 165/10; 165/47; 366/130; 220/592.09
(58) Field of Classification Search ............. 165/104.17, 165/10; 219/209, 210, 385–387, 521
See application file for complete search history.

(56) References Cited

U.S. PATENT DOCUMENTS

| | | | | |
|---|---|---|---|---|
| 3,764,780 A | * | 10/1973 | Ellis | 219/430 |
| 4,162,671 A | * | 7/1979 | Christy | 126/400 |
| 4,641,974 A | * | 2/1987 | Church | 366/342 |
| 5,544,960 A | * | 8/1996 | Sommovigo et al. | 366/130 |
| 6,653,138 B1 | * | 11/2003 | Turner et al. | 506/11 |
| 6,672,370 B2 | * | 1/2004 | Searls et al. | 165/10 |
| 2002/0027147 A1 | | 3/2002 | Inaba et al. | 3/2 |
| 2004/0186541 A1 | * | 9/2004 | Agarwal et al. | 607/114 |
| 2007/0077657 A1 | * | 4/2007 | Carlson et al. | 436/4 |

FOREIGN PATENT DOCUMENTS

JP        11-113560      4/1999

* cited by examiner

*Primary Examiner* — Allen Flanigan
(74) *Attorney, Agent, or Firm* — Mattingly & Malur, PC

(57) ABSTRACT

A temperature regulating member capable of avoiding deterioration in heat dissipation efficiency of a heat-accumulating material, and deterioration in a buffer function thereof, due to ununiformity in heat distribution inside the heat-accumulating material. With the use of a churning flow occurring by disposing one piece of stirrer or plural stirrers inside the heat-accumulating material, and by causing a relative position of the stirrer, inside the heat-accumulating material, to be changed during transportation, it is possible to eliminate ununiformity in heat distribution inside the heat-accumulating material. The temperature regulating member has a feature in that a phenomenon of a peripheral part of the heat-accumulating material being first cooled to be subsequently solidified is avoided, thereby enabling the heat dissipation efficiency and the buffer function to be maintained.

11 Claims, 3 Drawing Sheets

TEMPERATURE REGULATING MEMBER

CLAIM OF PRIORITY

The present application claims priority from Japanese application JP 2006-210462 filed on Aug. 2, 2006, the content of which is hereby incorporated by reference into this application.

FIELD OF THE INVENTION

The present invention relates to a temperature regulating member for use in the case of, for example, transporting cells or like, kept substantially at a predetermined temperature.

BACKGROUND OF THE INVENTION

In the case of a sample of cells or like, a change occurs to a load according to a temperature condition. Accordingly, temperature control is often required when transporting the sample of the cells or like. For example, there is a demand for transportation of cells kept at a temperature on the order of 36° C., higher than an ordinary outdoor air temperature, and close to a body temperature.

Meanwhile, a method for managing temperature of a liquid phase substance includes, for example, a method whereby a stirrer rotatable by magnetism is placed in a vessel containing a liquid (for example, JP-A No. 11 (1999)-113560). This is a method whereby a stirrer is embedded in a liquid phase substance contained in a vessel so as to be rotated by magnetism to generate a churning flow, thereby supplying a homogeneous culture medium.

SUMMARY OF THE INVENTION

Ambient temperature can be controlled by use of a heat-accumulating material with a hydrocarbon (paraffin, and so forth) undergoing liquid-to-solid phase transition at around 36° C., sealed therein. When a sample of cells or like, covered with the heat-accumulating material, is transported, the heat-accumulating material not only serves as a heat source, but also has a buffer function as it is in liquid state. If the heat-accumulating material is surrounded with a heat-insulating material to be then housed in an external vessel (such a configuration is hereinafter called as a transport vessel), this will enable the ambient temperature of the sample to be maintained constant around 36° C. for many hours.

Because heat dissipation occurs to a peripheral part of the heat-accumulating material, in contact with an outside air lower in temperature than the interior thereof, gradual solidification starts from the peripheral part thereof, in liquid state. At this point in time, the peripheral part of the heat-accumulating material is first cooled along with the heat dissipation to be subsequently solidified. Because heat dissipation efficiency is proportional to a temperature difference between the outside air, and the peripheral part of the heat-accumulating material, as the temperature difference between the outside air, and the peripheral part of the heat-accumulating material becomes smaller due to cooling of the peripheral part of the heat-accumulating material, so does lower the heat dissipation efficiency, whereupon heat will be left out within the heat-accumulating material. As a result, there occurs a decrease in time length for maintaining an inner temperature of the transport vessel. Further, since the peripheral part of the heat-accumulating material undergoes solidification early on, the buffer function as well will be lost.

If a churning flow is caused to occur inside the heat-accumulating material by any means, a portion of the heat-accumulating material, at the peripheral part thereof, having lost heat, will be immediately drawn toward inner parts of the heat-accumulating material, so that heat distribution inside the heat-accumulating material will become uniform. It does not happen that solidification occurs only to molecules positioned on the peripheral part thereof. It is therefore possible to avoid solidification of only the peripheral part of the heat-accumulating material, due to cooling thereof, and to concurrently maintain the buffer function provided that the churning flow exists.

In the case of adopting the method described as an example with reference to Patent Document 1, since the stirrer embedded in the liquid phase substance beforehand is rotated by magnetism, the churning flow can be generated. In order to cause rotation of the stirrer, there is the need for a magnetic agitator to provide a drive power for producing a rotating magnetic field, and in order to activate the magnetic agitator, there is the need for a drive unit made up of a battery and an electrical circuit. Granting that the drive unit can be installed in the transport vessel for use in transportation of the cells, the transport vessel will increase in size in order to secure space necessary for installation of the drive unit, so that temperature adjustment will be difficult to implement, and the transport vessel itself will become heavier, and more expensive. Furthermore, because an electrical drive unit will be inoperable in case that the battery runs down, or the electrical circuit is out of order, there is a possibility that it is difficult to guarantee reliable operation in the course of transportation over many hours. It is therefore an object of the invention to enhance the heat dissipation efficiency of the heat-accumulating material, and maintenance of the buffer function thereof by use of inexpensive means small in size, and light in weight.

In order to resolve the problem described, the invention proposes the following means.

A stirrer that does not react with a heat-accumulating material is disposed in the heat-accumulating material. More specifically, one piece of stirrer of a certain magnitude in size and mass, or plural pieces of the stirrers are preferably embedded in the heat-accumulating material beforehand. The stirrers each may be in a shape enabling a relative position of the stirrer in the heat-accumulating material to be readily changed during transportation (any shape among a spherical shape, cylindrical shape, conical shape, and a cubic shape formed by combination thereof). A constituent material of the stirrer may be any material (for example, glass, metal such as iron, and so forth) that does not react with the hydrocarbon sealed in the heat-accumulating material, and can smoothly move about without undergoing mutual reaction. The stirrer can readily change the relative position thereof, in the heat-accumulating material, due to tilt, vibration, sway, and so forth, to which the transport vessel is subjected during the transportation of the transport vessel. A churning flow occurs to the hydrocarbon in liquid state, sealed in the heat-accumulating material, due to changes in the position of the stirrer, so that uniform heat distribution is attained. For the heat-accumulating material, use is made of paraffin, one of saturated straight chain hydrocarbons expressed by a general formula $C_nH_{2n+2}$. In particular, use is made of, for example, n-Eicosane expressed by a chemical formula $C_{20}H_{42}$, having a melting point at 36.4° C.

Parts of a vessel for containing the heat-accumulating material, in contact with a culture vessel where cells are cultivated, may be formed of a film-like material having elasticity, and capable of securing a position of the culture vessel.

Further, for the parts of the vessel, in contact with the culture vessel, use may be made of material high in thermal conductivity, and for other parts of the vessel, use may be made of a heat-insulating material. In this case, it is possible to adjust efficiency of thermal conduction to the cells. For a constituent of the stirrer, use can be made of glass, and so forth.

Since a drive force using electricity, and so forth is not required by a method for controlling an ambient temperature by use of the heat-accumulating material provided with the stirrer, the transport vessel remains the same in size, and the temperature of the vessel as a whole can be controlled with greater ease while transportation can be simplified.

With the invention, it is possible to cause the churning flow to occur inside the heat-accumulating material during transportation. As a result, temperature inside the heat-accumulating material becomes uniform, so that it is possible to avoid a state where only the peripheral part of the heat-accumulating material is cooled early on to be subsequently solidified. Further, since a temperature difference from the ambient temperature is maintained, heat dissipation efficiency of the heat-accumulating material is kept at a high level. Furthermore, since the peripheral part of the heat-accumulating material is held in liquid state for a long duration, a buffer function thereof can be maintained for many hours.

DETAILED DESCRIPTION OF THE PREFERRED EMBODIMENTS

Figure 1:
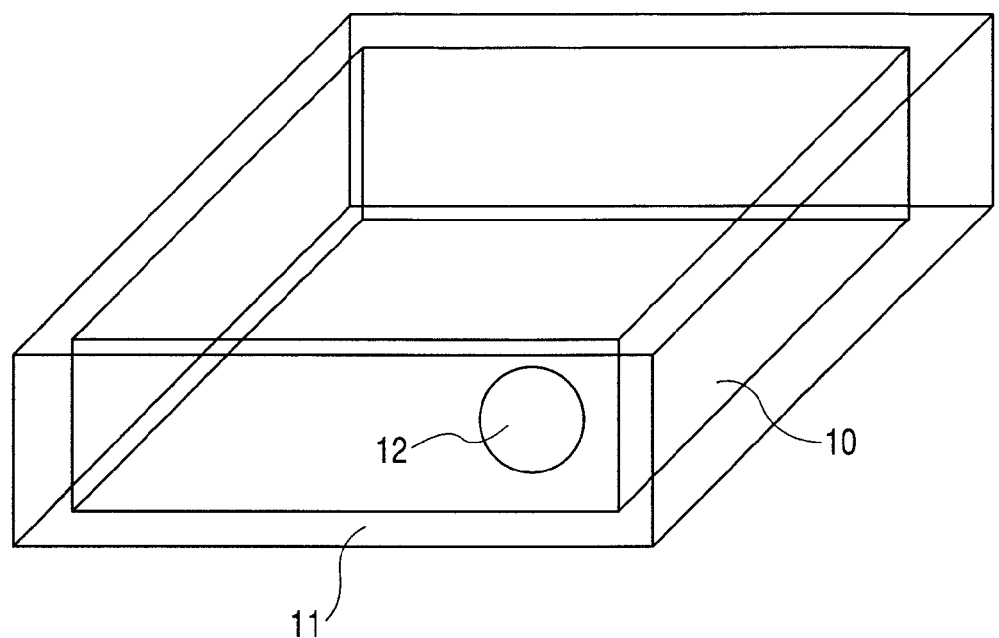
FIG. 1 is a perspective view of an embodiment of a temperature regulating member according to the invention, showing one piece of stirrer, and a heat-accumulating material.
Figure 2:
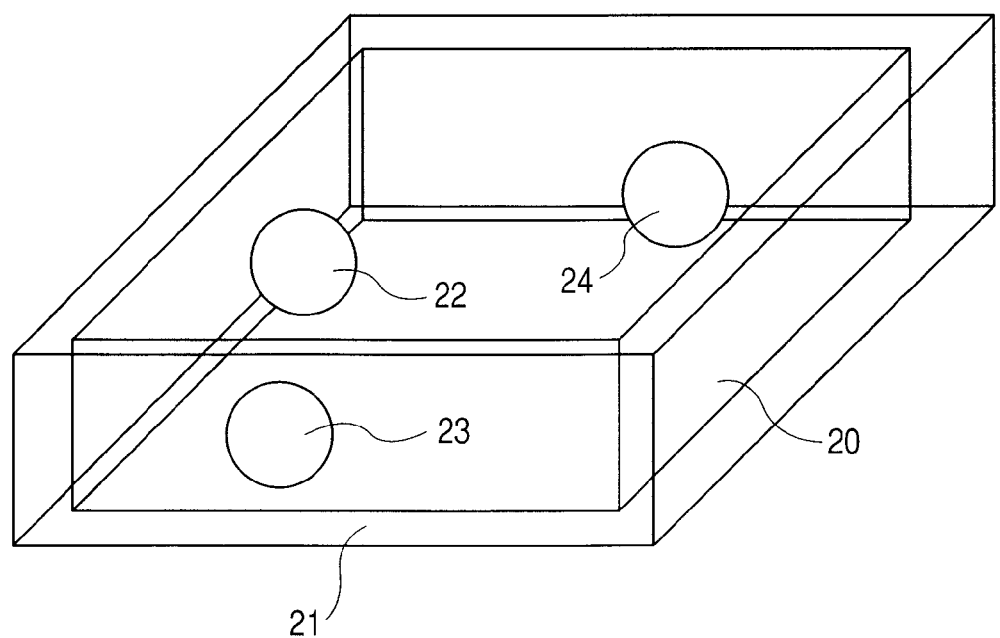
FIG. 2 is a perspective view of another embodiment of a temperature regulating member according to the invention, showing 3 pieces of stirrers and a heat-accumulating material.
Figure 3:
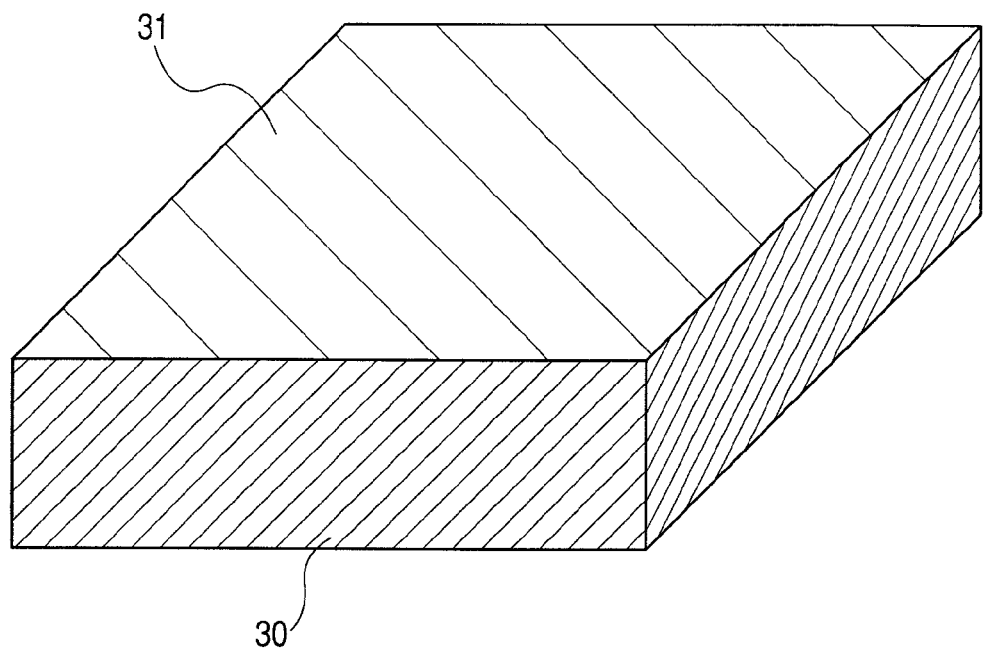
FIG. 3 is a perspective view of still another embodiment of a temperature regulating member according to the invention, comprising stirrers, and a heat-accumulating material with improved thermal conductivity.
Figure 4:
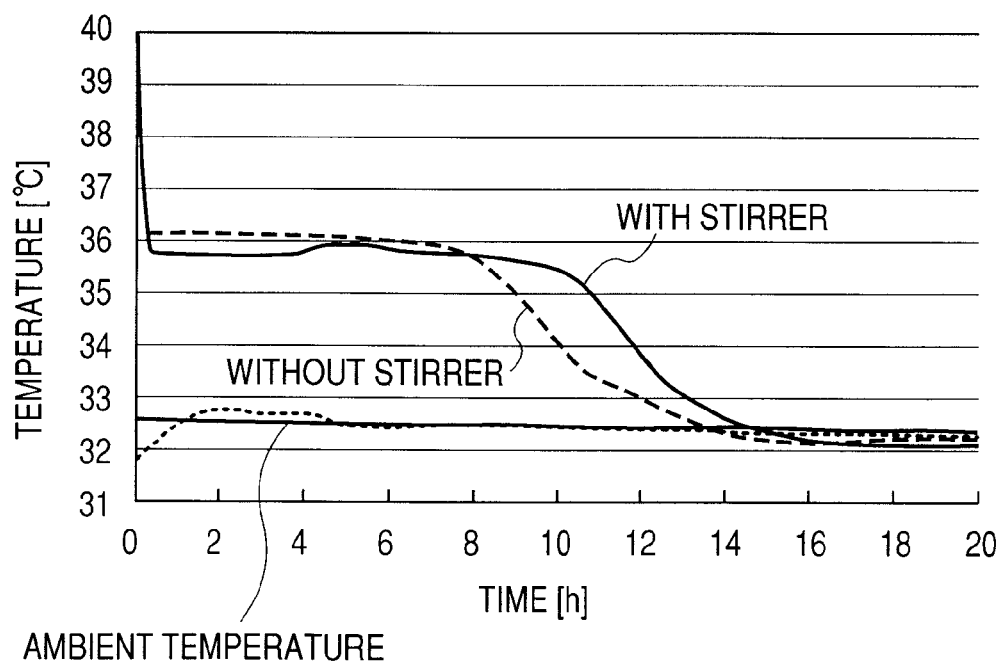
FIG. 4 is a diagram showing results of evaluation on time-dependent variations in temperature as measured with respect to the case where a stirrer was embedded in comparison with the case where the stirrer was not used.
Figure 5:
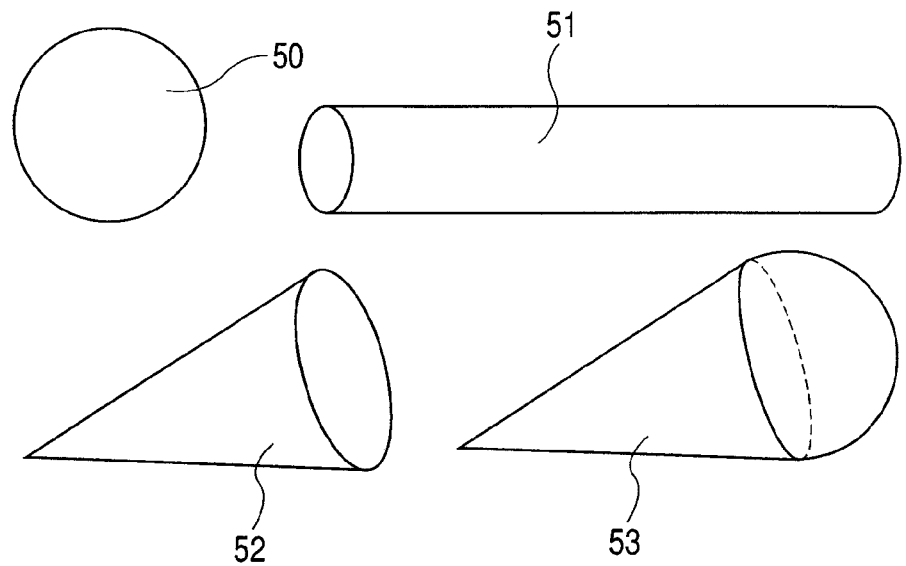
FIG. 5 is a schematic illustration showing shapes of the stirrers.
Figure 6:
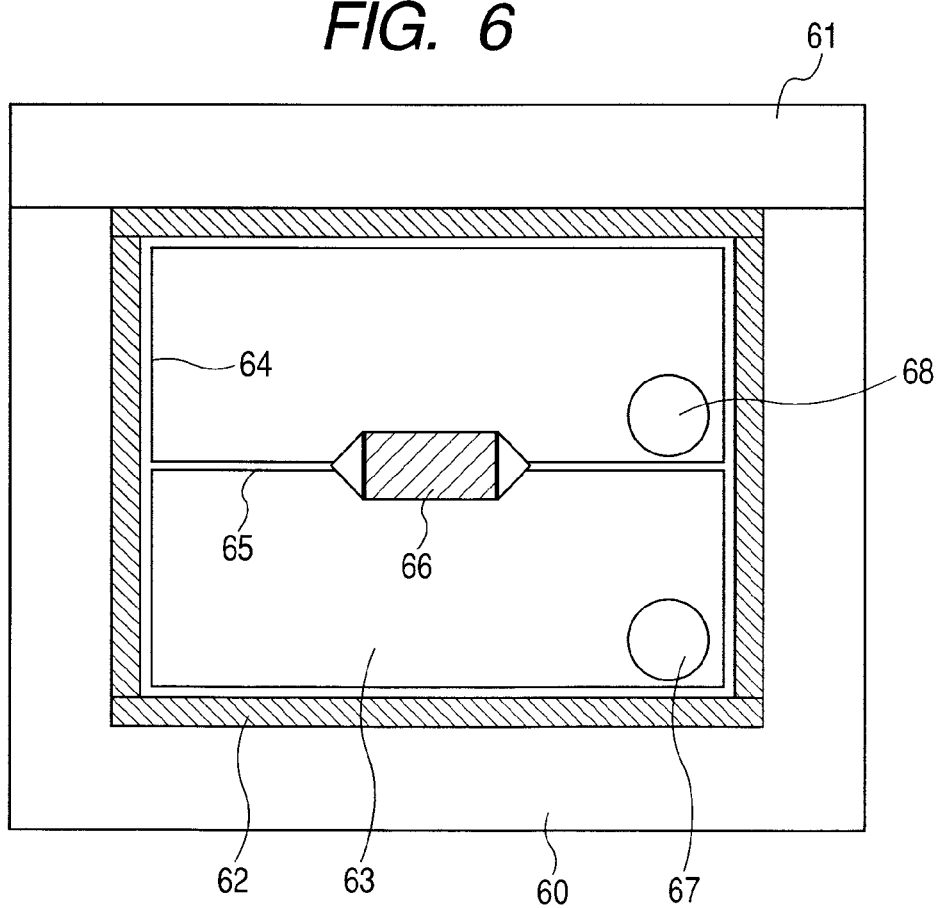
FIG. 6 is a schematic illustration showing a configuration of a transport vessel.

Embodiments of the invention will be described hereinafter with reference to the accompanying drawings. FIG. 1 is a perspective view showing an embodiment of a temperature regulating member according to the invention, comprising a heat-accumulating material, a stirrer disposed within the heat-accumulating material, and a vessel containing the heat-accumulating material, and the stirrer. FIG. 2 is a perspective view of another embodiment of a temperature regulating member according to the invention, comprising a heat-accumulating material, plural (3 pieces in this embodiment) stirrers disposed within the heat-accumulating material, and a vessel containing the heat-accumulating material, and the stirrers. FIG. 3 is a perspective view of still another embodiment of a temperature regulating member according to the invention, wherein parts of a vessel containing a heat-accumulating material, in contact with a culture vessel containing cells, are formed of a thermally conductive member 30 made of material high in thermal conductivity, and remaining parts thereof are formed of a heat-insulating material 31 to thereby enhance a heat dissipation efficiency. FIG. 4 is a diagram showing a process whereby heat of the heat-accumulating material undergoes dissipation along with the elapse of time, and temperature of the heat-accumulating material comes to match an ambient temperature with respect to the case where the stirrer is used in comparison with the case where the stirrer is not used. FIG. 5 is a schematic illustration showing shapes of the stirrers. FIG. 6 is a schematic illustration showing a configuration of a transport vessel comprised of the temperature regulating member, and a heat insulation part, housing the culture vessel therein.

Referring to FIG. 1, there will be described respective configurations of the heat-accumulating material, and the stirrer. A vessel 11 for enclosing a solid hydrocarbon (n-Eicosane) 10 serving as a heat source is provided, and the stirrer 12 spherical in shape is embedded inside the vessel 11. As to a shape of the vessel 11, a cuboidal shape is shown in the figure by way of example. The stirrer 12 is disposed so as to come into contact with the hydrocarbon.

In FIG. 2, three pieces of stirrers 22, 23, 24 are embedded in the heat-accumulating material in connection with a configuration of the temperature regulating member shown in FIG. 1. In the figure, there is shown the case where three pieces of the stirrers are embedded by way of example since use of plural pieces of the stirrers is presumed.

In FIG. 3, the vessel 11 is replaced with a vessel formed of the heat-insulating material 31 in combination with the thermally conductive member 30 made of the material high in thermal conductivity, in connection with the configuration of the temperature regulating member shown in FIG. 1. The vessel is made up of a heat-insulating wall 31, and a thermally conductive film 30. The thermally conductive film 30 will come into contact with a culture vessel containing cells, disposed in an upper part thereof, during transportation, and heat conduction occurs thereto through the thermally conductive film 30, so that temperature of the culture vessel is maintained around 36° C. No heat dissipation occurs to any other parts due to heat insulation by the agency of the heat-insulating wall 31, thereby avoiding waste of heat dissipation. A stirrer is embedded inside the vessel. In the figure, use of one piece of the stirrer is presumed; however, as in the case shown in FIG. 2, plural pieces (for example, 3 pieces) of the stirrers may be embedded.

FIG. 4 is a diagram showing results of evaluation on time-dependent variations in temperature at the peripheral part of the heat-accumulating material by way of example as measured with respect to the case where 2 pieces of the stirrers were embedded beforehand in comparison with the case where the stirrer was not used. The evaluation was made with an ambient temperature at 32° C. The greater the number of the stirrers, the more intense the churning flow occurring inside the vessel will be. Further, as progress toward solidification is made, degree of freedom of the stirrers becomes smaller, and the greater the number of the stirrers, the longer a length of time until movements of all the stirrers will come to a stop becomes longer on a probabilistic basis, so that the churning flow will continue for longer time as compared with the case where the number of the stirrers is just one. On the other hand, if the number of the stirrers increases, a quantity of the hydrocarbon for use as the heat source, to be enclosed in the vessel, will be decreased to an extent corresponding thereto, resulting in a smaller heat storage amount. Accordingly, with the present embodiment, 2 pieces of the stirrers were used.

With this working example, use was made of a vessel about 10 cm×10 cm×3 cm in size, containing the heat-accumulating material, and 2 pieces of the stirrers each in the shape of a sphere about 1 cm in diameter were embedded in the vessel. The stirrers each were made of glass, and were freely movable without undergoing mutual reaction with the solid hydrocarbon enclosed, to serve as a heat source. There was prepared a temperature regulating member of the same configuration except that the stirrer was not embedded in the vessel, the heat-accumulating material was heated up by a thermostat at 45° C. beforehand to thereby melt the hydrocarbon enclosed therein so as to be in a liquid state, and subsequently, the temperature regulating member was put in a state where the same is subjected to mild tilting and rotational movement under an ambient temperature at 32° C. The mild tilting and rotational movement were intended to re-create a model of movement at the time of transportation. Measurements were taken on variations in the temperature at the peripheral part of the heat-accumulating material by use of a temperature sensor during this time period. Then, an evaluation was made on solidification states of the heat-accumulating material, and the time-dependent variations in the temperature at the peripheral part of the heat-accumulating material by comparing the case where the stirrer was used with the case where the stirrer was not used.

Rapid drop in temperature occurred to the heat-accumulating material that was heated up by the thermostat at 45° C. beforehand regardless of whether or not the stirrer was present when exposed to the ambient temperature at 32° C., and the heat-accumulating material was found in a constant state at around 36° C., which is a melting point of the hydrocarbon. Thereafter, solidification started from the peripheral part of the heat-accumulating material in the case where the stirrer was not present. On the other hand, in the case where the stirrer was present, it was observed that there occurred a few small clusters due to solidification of the heat-accumulating material, however, the stirrer continued movement inside the vessel for longer hours than in the case where the stirrer was not present, and it did not happen that the peripheral part only underwent solidification. Thus, it was exhibited that the heat-accumulating material in whole was kept in liquid state for many hours, and was capable of maintaining the buffer function for lessening the impact of a shock to the culture vessel, anticipated during transportation. As for the time-dependent variations in the temperature at the peripheral part, it was confirmed that temperature holding time was increased by 11.6% as compared with the case where the stirrer was not present. It is therefore exhibited that the present method has contributed to enhancement in the heat dissipation efficiency of the heat-accumulating material, and in the buffer function thereof. In consequence, with the present method, it is possible to increase transportation time of the transport vessel when a given temperature can be substantially maintained, and to maintain the buffer function for many hours by keeping the heat-accumulating material in liquid state for many hours.

FIG. 5 is the schematic illustration showing the stirrers in various shapes. The stirrers each are in a shape enabling a relative position of the stirrer in the heat-accumulating material to be readily changed, including a spherical stirrer 50, a cylindrical stirrer 51, a conical stirrer 52, and a stirrer 53 as a cubic example of combination thereof, made up by combining a cone with a sphere. The stirrer capable of most readily changing a relative position thereof in the heat-accumulating material is the spherical stirrer 50.

FIG. 6 is a schematic illustration showing the configuration of the transport vessel with the culture vessel housed therein. The transport vessel is made up of an external vessel 60 and a lid 61. The heat insulation part 62 is disposed on the inner side of the transport vessel to fulfill a function of preventing heat from leaking to the outside. Reference numeral 63 denotes a heat-accumulating material and an external part thereof is surrounded with a heat insulation wall 64, and a thermally conductive film 65 having elasticity, and high in thermal conductivity. Reference numerals 67, 68 each denote a stirrer. The stirrers each may be in the shape described as above. The thermally conductive film 65 also has a function of a vessel where the heat-accumulating material, and the stirrers are enclosed. The heat-accumulating material is stored in two stages, and a culture vessel 66 with cells or the like, contained therein, is stored between the respective heat-accumulating materials, in the two stages. The culture vessel 66 is in contact with the heat-accumulating material from all directions through the intermediary of the thermally conductive film 65. Accordingly, temperature can be maintained by the agency of the heat-accumulating material while the heat-accumulating material in liquid state can fulfill the function of a buffer material.

What is claimed is:

1. A temperature regulating member that can be transported comprising: a first vessel for housing having a culture vessel housed therein, heat-accumulating material undergoing a liquid-to-solid phase transition at a given temperature disposed inside said first vessel in plural stages within said first vessel; a stirrer disposed so as to be in contact with the heat-accumulating material, for stirring up the heat-accumulating material; and a thermally conductive film having elasticity, and disposed so as to surround the culture vessel; wherein the stirrer is freely movably embedded in the heat-accumulating material whereby the stirrer stirs up the heat-accumulating material by freely changing its relative position in the heat-accumulating material solely by movement of the first vessel during transport without using a drive unit, and wherein the culture vessel contacts the heat-accumulating material through the thermally conductive film and the thermally conductive film secures a position of the culture vessel in the first vessel at a position between the two stages.

2. The temperature regulating member according to claim 1, wherein the heat-accumulating material is paraffin.

3. The temperature regulating member according to claim 2, wherein the paraffin is n-Eicosane.

4. The temperature regulating member according to claim 1, comprising a plurality of the stirrers.

5. The temperature regulating member according to claim 1, wherein the vessel comprises a heat insulation part, and a thermally conductive material part.

6. The temperature regulating member according to claim 1, wherein the stirrer is made of glass.

7. A transportable holding vessel comprising: a first vessel having a culture vessel housed therein; a heat-accumulating material undergoing a liquid-to-solid phase transition at a given temperature disposed inside said first vessel in plural stages within said first vessel; a stirrer disposed inside said first vessel so as to be in contact with the heat-accumulating material, for stirring up the heat-accumulating material; a heat insulation part disposed so as to surround the first vessel; and an external vessel for housing the first vessel, and the heat insulation part; and wherein the stirrer is freely movably embedded in the heat-accumulating material whereby the stirrer stirs up the heat-accumulating material by freely changing its relative position in the heat-accumulating material solely by the movement of the vessel during transport without using a drive unit, and wherein the at least a part of the first vessel is formed of a thermally conductive film having elasticity, and the thermally conductive film is disposed so that it surrounds the culture vessel and secures a position of the culture vessel in the vessel at a position between the two stages.

8. The transportable holding vessel according to claim 7, wherein the heat-accumulating material is paraffin.

9. The transportable holding vessel according to claim 8, wherein the paraffin is n-Eicosane.

10. The temperature regulating member according to claim 1, wherein the stirrer is formed from among a spherical shape, a cylindrical shape, a conical shape and a cubic shape or by a combination thereof.

11. The transportable holding vessel according to claim 7, wherein the stirrer is formed from among a spherical shape, a cylindrical shape, a conical shape and a cubic shape or by a combination thereof.

* * * * *